United States Patent [19] [11] 4,405,654
Lee [45] Sep. 20, 1983

[54] 4'-HALO-SUBSTITUTED SUCROSE DERIVATIVES

[75] Inventor: Cheang K. Lee, Singapore, Singapore

[73] Assignee: Tate & Lyle Public Limited Company, England

[21] Appl. No.: 371,995

[22] Filed: Apr. 26, 1982

Related U.S. Application Data

[63] Continuation-in-part of Ser. No. 315,479, Oct. 27, 1981, abandoned.

[30] Foreign Application Priority Data

Oct. 28, 1980 [GB] United Kingdom ............... 8034666
Aug. 21, 1981 [GB] United Kingdom ............... 8125621

[51] Int. Cl.³ ...................... A23G 3/30; A23L 1/236; A61K 7/16; C07H 5/02
[52] U.S. Cl. ........................................ 426/658; 426/3; 426/548; 426/590; 424/48; 424/49; 424/180; 536/122
[58] Field of Search ............... 536/122; 426/548, 658, 426/3, 590; 424/48, 49, 180

[56] References Cited

U.S. PATENT DOCUMENTS 4,343,934  8/1982  Jenner et al. ...................... 426/658

FOREIGN PATENT DOCUMENTS 1543167  3/1979  United Kingdom .
2079749  1/1982  United Kingdom ............... 536/122

Primary Examiner—Raymond N. Jones
Assistant Examiner—Elizabeth J. Curtin
Attorney, Agent, or Firm—Ostrolenk, Faber, Gerb & Soffen

[57] ABSTRACT

Compounds of the general formula (I)

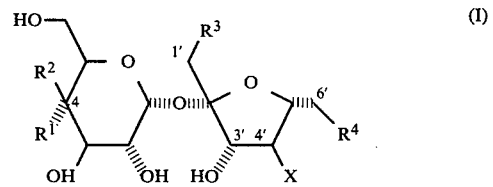

(wherein X represents a halogen atom;
$R^1$ and $R^2$ respectively represent a combination selected from the group consisting of: a hydroxy group and a hydrogen atom; a halogen atom and a hydrogen atom; and a hydrogen atom and a halogen atom; and
$R^3$ and $R^4$, which may be the same or different, each represent a substituent selected from the group consisting of a halogen atom and a hydroxy group;
at least one of $R^1$, $R^2$ and $R^3$ representing a halogen atom) are potent sweeteners obtainable by opening a corresponding 3',4'-lyxoepoxide with a source of halide ions.

12 Claims, 1 Drawing Figure

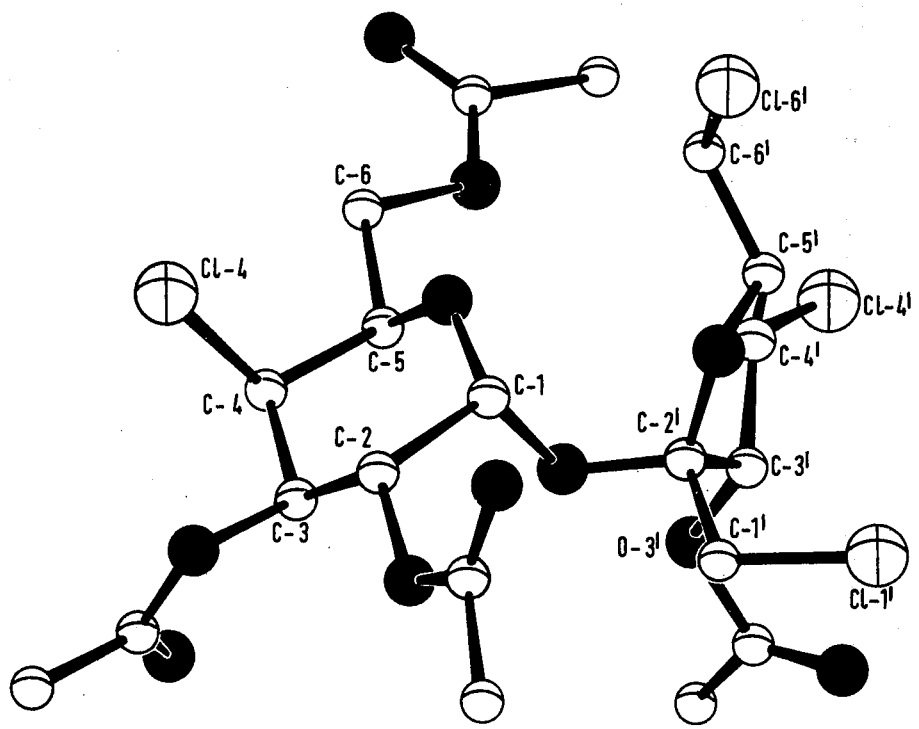

4'-HALO-SUBSTITUTED SUCROSE DERIVATIVES

This application is a continuation-in-part of application Ser. No. 315,479 filed Oct. 27, 1981, now abandoned.

This invention relates to new compounds derived from sucrose which are high potency sweeteners. The invention also relates to compositions containing the sweeteners and to sweetening methods using them.

Although sucrose is still the most widely used sweetening agent, many efforts have been made to find substantially sweeter alternatives which could be used when it is desired to combine a high degree of sweetness with a low calorie content and/or a low risk of dental caries, e.g. in dietetic products and in the manufacture of soft drinks. The two most commercially successful non-sucrose sweeteners (that is to say sweeteners comprising a compound other than sucrose itself) to date have been saccharin and cyclamate, having respectively about 200 and about 30 times the sweetening power of sucrose. However, the use of these sweeteners, particularly cyclamate, has recently been restricted or banned in some countries because of doubts about their safety. Saccharin also suffers from the disadvantage of an unpleasantly bitter after-taste which can be detected by many people.

More recently, many other non-sucrose sweeteners have been investigated, some of natural origin and others synthetic, covering a wide range of chemical structures. These compounds have included proteins such as monellin, thaumatin and miraculin; dipeptides such as aspartame, and dihydrochalcones such as neohesperidin dihydrochalcone. However, apart from the difficulties of synthesising or extracting such sweeteners, there is the problem that they do not necessarily possess the same quality sweetness as sucrose. In particular, as compared with sucrose, the sweetness may be slow in onset and relatively lingering, and there may be a licorice-like or other after-taste, making the sweeteners unsuitable as a direct replacement for sucrose unless these differences can be masked.

Although numerous sweeteners of widely diverse chemical structures have now been investigated, it is significant to note that sweetness substantially greater than that of sucrose has been discovered in only one very small group of derivatives of sucrose and in no other simple carbohydrate. Those intensely sweet substances that are known are generally not carbohydrates at all. Indeed, the presence of some substituents on the sucrose molecule is known to destroy its sweetness. Thus, for example, chlorination at 6 and 6', or amination in various positions yields products which are non-sweet. The loss of sweetness in sucrose derivatives in which hydroxy groups were replaced by other functions confirmed the theory of Shallenberger (J.Food Sci.(1963) 28, 584) that sweetness of sugars was caused by hydrogen bonding of suitably placed hydroxy groups with the receptor site. Research in support of this theory was carried out by various workers by removing the hydroxy groups from sucrose and by altering their configuration. In every case, removal of hydroxy groups either reduced sweetness or left is substantially unaltered.

Then, towards the end of 1975, some very sweet sucrose derivatives were discovered. British Pat. No. 1 543 167 discloses and claims a particular class of chlorinated derivates of sucrose which were found to possess a high degree of sweetness, in some instances several hundred times that of sucrose, and yet to have the same quality of sweetness as sucrose with the absence of any delay in onset or unpleasant after-taste. The compounds in British Pat. No. 1 543 167 have the hydroxy groups at certain combinations of the 4-, 6-, 1'-, and 6'-positions replaced by chlorine atoms. A particularly interesting compound is 4,1',6'-trichloro-4,1',6'-trideoxygalactosucrose, hereinafter referred to as TGS. The positioning of the chloro substituents was found to be critical in that only certain combinations of chloro substituents gave sucrose derivatives with a high degree ofsweetness: other combinations removed the sweetness of sucrose as would have been expected.

In the years following 1975, no further very sweet derivatives of sucrose have been discovered. Indeed, the only further chlorinated derivatives of sucrose assessed in that time are the 2,1'-dichloro-2,1'-dideoxy derivative, 2, 1'-dideoxy derivative, which is not sweet at all, and the 2,6,1',6'-tetrachloro-2,6,1', 6'-tetradeoxy derivative disclosed in U.K. Patent application No. 2037561A. In complete contrast to the compounds of British Pat. No. 1 543 167, this 2,6,1',6'-tetrachloro-derivative of sucrose was found to be a potent bittering agent, having a bittering power comparable with that of quinine. It thus appeared that departure from the chlorine substitution of the British Pat. No. 1 543 167 would lead to compounds which are not sweet but which might instead possess other organoleptic properties.

Very surprisingly, a new family of halosucrose derivatives has been found possessing a different pattern of halogen-substitution but nevertheless possessing an intense sweetness. These new compounds are all 4'-halo-substituted.

According to the present invention there are provided compounds of the general formula

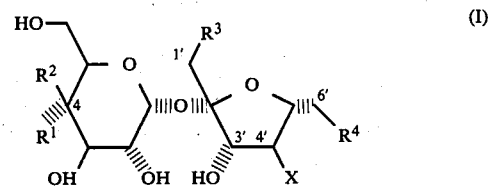

(in which

X represents a halogen atom;

$R^1$ and $R^2$ respectively represent a combination selected from the group consisting of: a hydroxy group and a hydrogen atom; a halogen atom and a hydrogen atom; and a hydrogen atom and a halogen atom; and $R^3$ and $R^4$, which may be the same or different, each represent a substituent selected from the group consisting of a halogen atom and a hydroxy group;

at least one of $R^1$, $R^2$ and $R^3$ representing a halogen atom.

The term 'halogen' is used herein to include chlorine, bromine, iodine and fluorine.

Halo-substitution at the 4-position is preferably provided by $R^2$ representing a halogen atom. The highest degree of sweetness is obtained when all the substituents $R^2$, $R^3$, $R^4$ and X represent halogen atoms.

These novel compounds have been found in informal taste tests to possess a degree of sweetness generally greater than corresponding 4'-hydroxy compounds, the 4'-halo substitution apparently enhancing the sweetness provided by halogen substitution elsewhere. Thus, in general, it is found that the sweetness of a halosucrose sweetener halo-substituted in at least one of the 4- and 1'-positions, and unsubstituted at the 4'-position, for example a chlorosucrose sweetener of British Pat. No. 1 543 167, is enhanced by incorporation of a 4'-halo-substituent. This sweetness has been evaluated by taste panels against dilute sucrose solutions. In a typical test, a 0.003% solution of the compound is compared by a panel of tasters with sucrose solutions at 5, 6, 7, 8 and 9% concentrations. The average sucrose concentration which matches the test solution is then divided by 0.003 to give the approximate number of times the test compound is sweeter than sucrose.

Compounds of Formula I of particular interest are:
(1) 4'-Bromo-4,1',6'-trichloro-4,1',4',6'-tetradeoxygalactosucrose (4-bromo-1,6-dichloro-1,4,6-trideoxy-$\beta$-D-fructofuranosyl 4-chloro-4-deoxy-$\alpha$-D-galactopyranoside);
(2) 4,1',4',6'-Tetrabromo-4,1',4',6'-tetradeoxygalacosucrose (1,4,6-trideoxy-$\beta$-D-fructofuranosyl 4-bromo-4-deoxy-$\alpha$-D-galactopyranoside);
(3) 4,1',4'-Trichloro-4,1',4'-trideoxygalactosucrose (1,4-dichloro-1,4-dideoxy-$\beta$-D-fructofuranosyl 4-chloro-4-deoxy-$\alpha$-D-galactopyranoside);
(4) 4,4',6'-Trichloro-4,4',6'-trideoxygalactosucrose (4,6-dichloro-4,6-dideoxy-$\beta$-D-fructofuranosyl 4-chloro-4-deoxy $\alpha$-D-galactopyranoside);
(5) 1',4',6'-Trichloro-1',4',6'-trideoxysucrose (1,4,6-trichloro-1,4,6-trideoxy-$\beta$-D-fructofuranosyl $\alpha$-D-glucopyranoside);
(6) 1,4,6-Tribromo-1,4,6-trideoxy-$\beta$-D-fructofuranosyl 4-chloro-4-deoxy-$\alpha$-D-galactopyranoside;
(7) 1,6-Dichloro-1,4,6-trideoxy-4-iodo-$\beta$-D-fructofuranosyl 4-chloro-4-deoxy-$\alpha$-D-galactopyranoside,
(8) 1',4'-Dichloro-1',4'-dideoxysucrose (1,4-dichloro-1,4-dideoxy-$\beta$-D-fructofuranosyl $\alpha$-D-glucopyranoside);
(9) 1,4,6-Trichloro-1,4,6-trideoxy-$\beta$-D-fructofuranosyl 4-deoxy-4-fluoro-$\alpha$-D-galactopyranoside; and
(10) 4,1',4',6'-Tetrachloro-4,1',4',6'-tetraceoxygalactosucrose (1,4,6-trichloro-1,4,6-trideoxy-$\beta$-D-fructofuranosyl 4-chloro-4-deoxy-$\alpha$-D galactopyranoside);

The sweetness of these compounds, when compared with a particular sucrose solution, is given below. For comprison, the sweetness of the corresponding chloro-substituted compound having a 4'-hydroxy group is also given.

| Compound No. | Sweetness (X sucrose) | % sucrose compared | comparison compound (X sucrose) |
|---|---|---|---|
| 1 | 3000 | 9 | 600 |
| 2 | 7500 | 9 | 600 |
| 3 | 220 | 8 | 120 |
| 4 | 160 | 8 | 40–50 |
| 5 | 100 | 5 | 70–80 |
| 6 | approx. 7000 | approx. 5–10 | 600 |
| 7 | approx 3500 | approx 5–10 | 600 |
| 8 | 30 | 0.6 | 20 |
| 9 | approx 200 | approx 5–10 | 600 |
| 10 | 2200 | 6.7 | 600 |

The compounds are found to be not only very sweet, but lack any unpleasant bitter, metallic or lingering aftertaste of the type associated with other potent sweetners. They are stable to heat and acid.

The new chloro-substituted compounds of formula (I) according to the present invention can be obtained by direct chlorination of a sucrose derivative blocked in the 6-position, e.g. by esterification, but free in at least the 4'-position and in at least one of the 4-, 1'- and 6'-positions, using sulphuryl chloride in the presence of an organic base such as pyridine and a suitable solvent, e.g. a chlorinated hydrocarbon such as chloroform. Some by-products, such as TGS, will also be formed in this reaction, and it is believed that the chlorination probably proceeds at the 4-, 1'- and 6'-positions more rapidly than at the 4'-. Alternatively, a sucrose derivative already carrying some chlorine atoms can be used as starting material, e.g. a 6-ester and 6-ether of TGS.

Preferably, the reaction is arranged so that the sulphur trioxide evolved from the reaction mixture is led out of the reaction vessel via a drying tube so as to prevent formation of sulphuric acid which might run back into the reaction mixture, e.g. with refluxing solvent. Typically, 8 molar equivalents of sulphuryl chloride are allowed to react with sucrose in pyridine/chloroform at about 40°–50° C. for several hours. The reaction mixture may be worked up as is usual for a sulphuryl chloride reaction, e.g. by quenching with methanol, dechlorosulphation with a trace of sodium iodide and acetylation followed by separation by chromatography, crystallisation etc.

However, the product obtained from this process, e.g. when applied to sucrose 6-acetate, has been found to comprise two configurational isomers on the 3' and 4' positions. While we do not wish to be bound by theory, it is believed that the epoxide formation can yield either the lyxo- or ribo-epoxides which in turn, on ring opening, yield the 4-chloro-4-deoxy-fructose and 4-chloro-4-deoxy-sorbose derivatives. For this reason, this method is not the method of choice, as the products must be subsequently separated and the yields are inevitably lower.

An alternative method of preparation for compounds of the general formula (ia) comprises the halogenation of a 4'-halo-4'-deoxysucrose derivative esterified or otherwise blocked in the 6-position and having a free hydroxy group in at least one of the 4- and 1'-positions. Any convenient halogenating agent may be used, for example sulphuryl chloride, or a Vilsmeier reagent, e.g. an N,N-dialkyl-(chloromethaniminium) chloride obtained by the reaction of an inorganic acid chloride with an N,N-dialkylformamide or N,N-dialkylacetamide, or carbon tetrabromide with triphenylphosphine. 4'-chloro-4'-deoxysucrose (i.e. 4-chloro-4-deoxy-$\beta$-D-fructofuranosyl $\alpha$-D-glucopyranoside) itself is a known compound (Guthrie et al. Carbohydrate Research 75(1979) pp C1 to C4).

However, the preferred method for the preparation of compounds of the general formula (I), is one in which the 4'-halo substituent is introduced into the fructo ring of a sucrose derivative without inversion of configuration, by formation of a 3',4'-lyxoepoxide; that is to say a process for the preparation of a compound of the general formula (I)

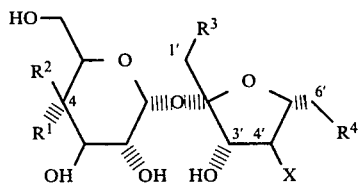

(in which

X represents a halogen atom;

$R^1$ and $R^2$ respectively represent a combination selected from the group consisting of: a hydroxy group and a hydrogen atom; a halogen atom and a hydrogen atom; and a hydrogen atom and a halogen atom; and $R^3$ and $R^4$, which may be the same or different, each represent a substituent selected from the group consisting of a halogen atom and a hydroxy group;

at least one of $R^1$, $R^2$ and $R^3$ representing a halogen atom) by (a) reacting a compound of the general formula (II)

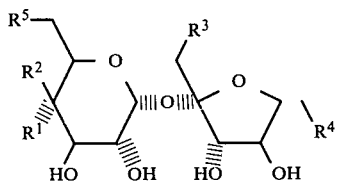

(wherein $R^1$ and $R^2$ respectively represent combination selected from the group consisting of a hydroxy group and a hydrogen atom; a protected hydroxy group and a hydrogen atom; a halogen atom and a hydrogen atom; and a hydrogen atom and a halogen atom;

$R^3$ and $R^4$, which may be the same or different, each represent a substituent selected from the group consisting of a halogen atom and a protected hydroxy group;

at least one of $R^1$, $R^2$ and $R^3$ representing a halogen atom; and $R^5$ represents a substituent selected from the group consisting of a hydroxy group and a protected hydroxy group) with a triarylphosphine together with a dialkyl azodicarboxylate to form a 3', 4'-lyxo-epoxide; (b) protecting all reactive hydroxy groups in the molecule; (c) reacting the epoxide with a source of halide ions; and (d) removing the protecting groups.

The process is conveniently effected using as the starting material a sucrose derivative in which halo substituents are present at those other positions required. Free hydroxy groups at the 3- and 6-positions lead to the formation in step (a) of unwanted 3,6-anhydro-byproducts and for this reason it is much preferred to protect one or both of these positions, e.g. by esterification or etherification, and of the two, the 6-position is the easier to protect (i.e. $R^5$ preferably represents a protected hydroxy group).

One particularly useful class of protected hydroxy groups in step (a) are the aryl- and/or alkyl-substituted silyloxy groups, for example the t-butyl-diphenyl-silyloxy group, the t-butyl-dimethylsilyloxy group and the t-butyl-diisopropylsilyloxy group. Other protected hydroxy groups include acyloxy groups, especially aliphatic or aromatic carboxylic acyloxy groups such as benzoyloxy groups or acetoxy groups, and also triarylmethoxy groups such as trityloxy groups.

Another class of protected hydroxy groups comprises alkylidenedioxy or aralkylidenedioxy groups, for example a 4,6-isopropylidenedioxy group, a 1,2:4,6-diisopropylidenedioxy system or a 4,6-benzylidenedioxy group.

The lyxoepoxide-forming reagent is a combination of a triarylphosphine such as triphenylphosphine with an activating azodicarboxylate diester, especially the diethyl ester (DEAD) and the diisopropyl ester (DIAD). At least one molar equivalent of the triarylphosphine is required, preferably with a small excess, and an amount of about 1.3 molar equivalents is very suitable. At least one and preferably two molar equivalents of the azodicarboxylate per molar equivalent of triarylphosphine is desirable, e.g. an amount of about 2.6 molar equivalents.

The lyxoepoxide forming reaction of step (a) is conveniently effected in an inert solvent, e.g. a hydrocarbon such as toluene, an ester such as ethyl acetate, or an amide such as dimethylformamide, depending on the solubility of the starting material. The reaction is mildly exothermic and the mixture may be maintained at ambient temperature or hotter (e.g. at reflux) for a suitable period of, say, 0.25 to 5 hours. Temperature regulation is more important if the 3- and 6- positions are unprotected. In that case, the mixture must be maintained cool. The reaction mixture may then be worked up by quenching with an alkanol, e.g. methanol, and separating the components, e.g. by chromatography.

The protection of the hydroxy groups in step (b) is conveniently effected by acylation, especially acetylation by reaction with acetic anhydride. It is also convenient that the protection at position 6 during the reaction with the source of chloride ions in step (c) should by acylation. Thus, if the 6- position has previously been protected with a silyl group, it is desirable to remove this and acylate instead in step (b). Alternatively, the hydroxy protection in step (b) can be afforded by formation of an ether, e.g. a tetrahydropyranyl ether.

The halogenation at the 4'-position is effected by opening the epoxide with a source of halide ions. For chlorination, it is preferred to use an aprotic solvent for the reactants, for example an amide such as dmf or an ether such as dioxan. The source of ions is conveniently a solvent-soluble chloride, such as lithium chloride. For bromination, similar conditions may be used, with the source of ions being a bromide such as lithium bromide. However, for higher yields it is preferable to use hydrogen bromide in dry acetic acid. Iodine can conveniently be introduced by reaction with a Grignard-type reagent, e.g. an alkylmagnesium iodide.

According to a further feature of the present invention, there are provided ingestible products and oral compositions containing at least one of the above mentioned novel compounds of the general formula (I) as a sweetening agent. By the term "ingestible product" there is meant one which in the ordinary course of use is intended to be swallowed, for instance a foodstuff or beverage, or an orally administered pharmaceutical composition. The term also includes concentrates for dilution to form ingestible products, e.g. "instant" foods and beverage mixes. By an "oral composition" there is meant one which in the ordinary course of use is not intended to be ingested as such, but is taken into the mouth for the treatment of the throat or buccal cavity, for instance a toothpaste, tooth powder, mouthwash, gargle, troche, dental lotion or chewing gum.

According to the present invention, there is also provided a sweetening composition comprising at least one of the above mentioned novel compounds together with a solid extender or carrier, or a liquid extender or carrier. By a "sweetening composition" there is meant a composition which is not itself taken orally, to be ingested or held in the mouth, but instead is intended to be added to other ingestible products or oral compositions to render them sweet, or to increase their sweetness. The extender or carrier referred to above comprises any suitable vehicle for the sweet compound so that it can be formulated in a composition which can conveniently be used for sweetening other products, e.g. granules, tablets or a solution in a dropper pack. The extender or carrier may thus include, e.g. conventional water-dispersible tabletting ingredients, such as starch, lactose and sucrose itself; low density bulking agents to provide a granular sweetening composition having a volume per unit sweetness equivalent to that of sucrose, e.g., spray dried maltodextrins; and aqueous solutions containing adjuvants such as stabilizing agents, colouring agents and viscosity-adjusting agents.

Beverages, such as soft drinks, containing the above-mentioned sweet compound may be formulated either as sugar-free dietetic products, or "sugar-reduced" products containing the minimum amount of sugar required by law. In the absence of sugar, it is desirable to add further agents to provide a "mouthfeel" similar to that provided by sugar, e.g. pectin or a vegetable gum. Thus, pectin may be added at a level of 0.1 to 0.15% in a bottling syrup.

According to a further feature of the present invention, there is provided a method of sweetening a substance comprising incorporating therein a novel compound of the general formula (I) mentioned above.

The following examples illustrate the invention further (temperatures are given in degrees centigrade; Amberlyst and Amberlite are registered Trade Marks):

EXAMPLE 1

4,1′,4′,6′-tetrachloro-4,1′,4′,6′-tetradeoxygalactosucrose (1,4,6-trichloro-1,4,6-trideoxy-β-D-fructofuranosyl 4-chloro-4-deoxy-α-D-galactopyranoside)

Route 1

A solution of TGS (10 g) in dry toluene (250 ml) was treated with DEAD (12 ml, 2.3 molar equiv) followed by TPP (19 g 1.3 m.e.). The reaction was exothermic, tlc (ether/petrol 7:1) after 5 min showed 2 major products. The mixture was refluxed 2.5 h. and then cooled and diluted with methanol (50 ml), concentrated to syrup, and taken up in ether. Most of the TPP oxide present was removed by crystallisation and the crude material was chromatographed on a column of silica gel (150 g), eluting with ether-light petroleum (1:1) to yield the 3,6-anhydro-3′,4∝-lyxoepoxide derivative of TGS (i.e., 3,6-anhydro-4-chloro-4-deoxy-α-D-galactopyranosyl 3,4-anhydro-1,6-dichloro-1,6-dideoxy-β-D-tagatofuranoside) (5 g, 55%) $[\alpha]_D^{20}$+6.5° (C,1.0, CHCl$_3$)

Anal: Calc. for C$_{12}$H$_{15}$O$_6$Cl$_3$: C: 39.83, H: 4.14, Cl: 29.46%, C: 40.28, H: 4.28, Cl: 26.45%.

Further elution of the column gave TGS 3′,4′-lyxoepoxide. This material was peracetylated by treatment with acetic anhydride, to give TGS 3′,4′-lyxoepoxide triacetate (i.e., 4-chloro-4-deoxy-2,3,6-tri-O-acetyl-α-D-galactopyranosyl 3,4-anhydro-1,6-dichloro-1,6-dideoxy-β-D-tagatofuranoside), side), structure supported by ′Hnmr and m.s. (see below).

Route 2

(a) TGS 6-t-butyldiphenylsilyl ether

A solution of TGS (8 g) in dry pyridine was treated with t-BDPS chloride (5.6 ml) and 4-dimethylaminopyridine (200 mg) at room temperature for 18 h. Tlc showed the presence of one major product together with some unreacted starting material (Tlc eluant ethyl acetate/acetone/10:10:1). The mixture was then poured into ice-water and extracted with ethyl acetate. The extracts were dried (Na$_2$SO$_4$) and evaporated to dryness. Crystallisation from ethanol gave TGS t-BDPS ether (10.5 g, 82.6%) m.p. 95°–97° (toluene-petrol), $[\alpha]_D^{20}$+39.3° (c 1.0 CHCl$_3$).

Anal: calc. C$_{28}$H$_{37}$O$_8$Cl$_5$Si: C: 52.87, H: 5.82, Cl: 16.75%, found: C: 52.28, H: 5.76.

(b) TGS 6-t-BDPS ether 3′,4′-lyxoepoxide

A solution of TGS t-BDPS ether (10 g) in dry toluene (250 ml) was treated with DEAD (12 ml,2.3 m.e.) followed by TPP (19 g, 1.3 m.e.). The reaction was exothermic Tlc after 5 min (ether/acetone, 10:1) showed one major product and the absence of starting material. The reaction mixture was diluted with methanol (50 ml) concentrated to syrup and taken up in ether. Most of the TPP oxide was removed by crystallization and the crude material was chromatographed on a column of dry silica gel (150 g) with ether/light petroleum (2:1), then gradually increasing polarity to 4:1 and finally with ether/acetone (9:1), to yield the epoxide (8.5 g, 87.6%).

(c) Peracetylation

Conventional acetylation of the product of stage (b) (7 g) using pyridine (70 ml) and acetic anhydride (7 ml) gave the diacetate (7.5 g, 94.8%) $[\alpha]_D^{20}$+104.5° (c 1.0, CHCl$_3$).

Anal: calc. for C$_{32}$H$_{39}$O$_9$Cl$_3$Si: C: 54.73; H: 5.55, Cl: 15.18%, found: C: 55.42, H: 5.76, Cl: 11.40%.

(d) TGS 3′,4′-lyxoepoxide triacetate

A solution of the diacetate from stage (c) (7 g) in tetrahydrofuran (150 ml) was treated with tetra-n-butylammonium fluoride (1.4 g) at room temperature for 18 h. Tlc (ether/light petroleum, 6:1) showed one major product with traces of slow moving products due to partial deacetylation. The mixture was concentrated, taken up in dry pyridine (50 ml) and treated acetic anhydride (7 ml) at room temperature for 3 h. Tlc ether/light petroleum (7:1) showed only one product. The reaction mixture was concentrated and was eluted from short column of silica gel (50 g) with ether/light petroleum (1:1) to give a crystalline product (4.3 g, 85.2%) identical with the product from Route 1, m.p. 133°–134° $[\alpha]_D^{20}$+116.3° (c 1.0, CHCl$_3$).

Anal. calc. for C$_{18}$H$_{23}$O$_{10}$Cl$_3$: C: 42.72, H: 5.54, Cl: 21.06%, found: C: 43.00, H: 4.58, Cl: 20.79%.

(e) 4,1′,4′,6′-tetrachloro-4,1′,4′,6′-tetradeoxygalactosucrose tetraacetate

A solution of the product from stage (d) in dmf (50 ml) was treated with lithium chloride (4 g ) at 90° for 5 h. The reaction mixture was poured into ice-water and extracted with ether. The extracts were dried (Na$_2$SO$_4$), concentrated to a syrup and acetylated in the normal manner with pyridine and acetic anhydride to yield the tetrachloro tetraacetate (2.6 g, 56.2%) m.p. 103°–104° (ether/light petroleum) $[\alpha]_D^{20}+75.0°$ (C, 1.0, CHCl$_3$).

Anal: calc: $C_{20}H_{26}O_{11}Cl_4$: C: 41.09, H: 4.45, Cl: 24.31%, found: C: 41.43, H: 4.53, Cl: 21.89.

(f)
4,1',4',6'-tetrachloro-4,1',4',6'-tetradeoxygalactosucrose

A solution of the tetraacetate from stage (e) (1.5 g) in dry methanol (25 ml) was treated with a catalytic amount of sodium methoxide at room temperature for 5 h, deionized by being stirred with Amberlyst 15 resin (T.M.) and concentrated to dryness. Crystallization from ether gave the product (1 g,93.5%) m.p. 58–60 $[\alpha]_D^{20}+72.3°$ (c 1.0,H$_2$O).

Anal: calc for $C_{12}H_{18}O_7Cl_4$: C: 34.61; H: 4.32; Cl: 34.13%, found: C: 35.5, H: 4.84, Cl: 34.2%.

Structure consistent with $^{13}$C nmr spectrum: $^{13}$C N.m.r. Chemical Shifts[a].

| Sucrose[b] | TGS | 4,1'4'6'tetrachloro 4,1'4'6' tetradeoxygalactosucrose |
|---|---|---|
| C-2' | 104.4 | 104.1 | 103.7 |
| C-1 | 92.9 | 93.5 | 93.1 |
| C-5' | 82.2 | 81.9 | 82.5 |
| C-3' | 77.4 | 76.9 | 77.7 |
| C-4' | 74.8 | 76.1 | 59.4 |
| C-5 | 73.2 | 71.4 | 71.0 |
| (C-3) | 73.5 | 68.8 | 68.5 |
| (C-2) | 71.9 | 68.4 | 68.1 |
| C-4 | 70.1 | 63.9 | 63.4 |
| C-1' | 63.3 | 45.6 | 44.3 |
| C-6' | 62.5 | 44.4 | 44.0 |
| C-6 | 61.2 | 62.2 | 61.8 |

[a]Chemical Shifts are expressed in p.p.m. downfield from the $^{13}$C N.m.r. resonance of tetramethylsilane. D$_2$O was used as solvent and D.S.S. as internal standard.

[b]Data from Development in Food Carbohydrates-2 C. K. Lee.

$^1$Hnmr parameters. First order chemical shifts (δ) and coupling constants (Hz) at 220 MHz.

|  | TGS 3'4' epoxide triacetate |  | TGS 3'4' epoxide 6t-BDPS ether diacetate |  |  | 4,1',4',6' tetrachloro-4,1',4',6'-tetradeoxy galacto sucrose |  |  |
|---|---|---|---|---|---|---|---|---|
| H-1 | 4.19 |  | 5.82d | $J_{1,2}$ | 3.2 | 5.80d | $J_{1,2}$ | 3.24 | 5.72d | $J_{1,2}$ | 3.5 |
| H-2 | 4.88 |  | 5.13dd | $J_{2,3}$ | 8.52 | 5.13dd | $J_{2,3}$ | 8.52 | 5.28dd | $J_{2,3}$ | 3 |
| H-3 | 4.69 |  | 5.31dd | $J_{3,4}$ | 2.94 | 5.35dd | $J_{3,4}$ | 2.94 | 5.28dd | $J_{3,4}$ | 2 |
| H-4 | 5.40 |  | 4.60t | $J_{4,5}$ | 1.18 | 4.71q | $J_{4,5}$ | 1.18 | 4.76d | $J_{4,5}$ | 2 |
| H-5 | 5.45 |  | 4.55td |  |  | 4.14m |  |  | 4.55m |  |  |
| H-6 |  |  |  |  |  |  |  |  |  |  |  |
| H-3' |  |  | 3.92d | $J_{3',4'}$ | 2.04 | 3.82d | $J_{3',4'}$ | 2.06 | 5.65d | $J_{3',4'}$ | 9 |
| H-4' |  |  | 3.90q | $J_{4',5'}$ | 2.22 | 3.79q | $J_{4',5'}$ | 2.52 | 4.37dd | $J_{4',5'}$ | 2 |
| H-5' |  |  | 4.18m |  |  |  |  |  | 4.32m |  |  |
| H-6' |  |  |  |  |  |  |  |  |  |  |  |
| H-1'a |  |  | 4.28d | $J_{1'a1'b}$ | 5.30 |  |  |  |  |  |  |
| H-1'b |  |  | 4.24d |  |  |  |  |  |  |  |  |

| Mass spectroscopic analysis | | |
|---|---|---|
| Compound No. | Hexopyranosyl cation m/e | Ketofuranosyl cation |
| 7 | 503 | 181(c) |

| Mass spectroscopic analysis | | |
|---|---|---|
| Compound No. | Hexopyranosyl cation m/e | Ketofuranosyl cation |
| TGS 6-t-BDPS | 247 (a) | 165 (c) |
| Ac$_2$ | 187 ↙ ↘ 205 | 129 (a) |
| 3'4' epoxide | 145 (a) 109 |  |
| 4 | 307 (a) | 181 (c) |
| TGS | 247 (a) | 165 (c) |
| (Ac)$_3$ | 187 (a) | 129 (a) |
| 3'4' epoxide | 145 (a) 109 |  |
| 8 | 307 (a) | 259 (b) |
| (Cl)$_4$(OAc)$_4$ | 247 (a) | 223 (c) |
|  | 187 (a) | 181 (c) |
|  | 145 (a) | 145 (a) |
|  | 109 |  |

(a) = 3:1 doublets 1 Cl
(b) = 27:27:9:1 quartet 3 Cl
(c) = triplet 2 Cl

X Ray Crystallographic Data

X-ray crystallographic of a crystalline sample of 4,1',4',6'-tetrachloro-4,1',4',6'-tetradeoxy galactosucrose tetraacetate gave the coordinates set forth in the set table:

The dimensions of the unit cell are: a=1.34 nm, b=0.94 nm, c=1.1 nm, $\beta=108.7°$ Monoclinic; space group P2$_1$.

A computer-generated view of the molecule is shown in the accompanying FIGURE, which clearly shows that the configuration at positions 3' and 4' is the fructo configuration.

ATOMIC CO-ORDINATES (X10$^4$) WITH ESTIMATED STANDARD DEVIATIONS IN PARENTHESES.
(position)

|  | X | Y | Z |
|---|---|---|---|
| CL(4) | 6370(1) | 2145(2) | 5341(1) |
| C(1) | 3987(3) | 2186(5) | 6598(4) |
| C(2) | 5127(3) | 2220(5) | 7481(4) |
| O(2) | 5213(3) | 2347(4) | 8806(3) |
| C(2,1) | 4887(4) | 1197(5) | 9340(5) |
| O(2,1) | 4454(3) | 180(4) | 8724(4) |
| C(2,2) | 5119(6) | 1411(9) | 10757(6) |
| C(3) | 5751(3) | 3456(5) | 7198(5) |
| O(3) | 6816(3) | 3281(4) | 7987(4) |
| C(3,1) | 7399(4) | 4473(6) | 8417(5) |
| O(3,1) | 7080(4) | 5641(5) | 8092(5) |
| C(3,2) | 8488(5) | 4069(9) | 9279(7) |

-continued

ATOMIC CO-ORDINATES (X10⁴) WITH ESTIMATED STANDARD DEVIATIONS IN PARENTHESES.

| (position) | X | Y | Z |
|---|---|---|---|
| C(4) | 5635(4) | 3542(5) | 5780(5) |
| O(5) | 3983(2) | 2220(3) | 5314(3) |
| C(5) | 4472(4) | 3464(5) | 4995(4) |
| C(6) | 4255(4) | 3441(5) | 3568(5) |
| O(6) | 3172(3) | 3905(5) | 3003(3) |
| C(6,1) | 2851(5) | 4174(7) | 1755(5) |
| O(6,1) | 3416(4) | 4052(8) | 1106(4) |
| C(6,2) | 1733(6) | 4666(13) | 1266(6) |
| O(1) | 3436(2) | 3373(3) | 6871(3) |
| CL(1') | 1143(1) | 2462(2) | 8333(1) |
| CL(4') | 387(1) | 5056(2) | 3799(1) |
| CL(6') | 1271(1) | −252(2) | 3908(1) |
| C(1') | 2409(4) | 2776(6) | 8190(5) |
| O(2') | 1902(2) | 1956(3) | 6053(3) |
| C(2') | 2358(3) | 3120(5) | 6845(4) |
| C(3') | 1701(4) | 4408(5) | 6218(4) |
| O(3') | 2225(3) | 5765(4) | 6499(4) |
| C(3',1) | 1908(4) | 6694(6) | 7249(5) |
| O(3',1) | 1309(5) | 6350(7) | 7777(6) |
| C(3',2) | 2397(6) | 8139(7) | 7282(7) |
| C(4') | 1450(4) | 4042(5) | 4819(4) |
| C(5') | 1205(3) | 2454(5) | 4820(4) |
| C(6') | 1415(4) | 1642(6) | 3749(5) |

EXAMPLE 2

1',4'-Dichlorosucrose (a) Silylation of 2,3,4,3',4'-penta-O-acetylsucrose(4-PAS)

A solution of 4-PAS (see, e.g. British Patent Specification No. 1 543 167) (20 g) in dry pyridine (100 ml) was treated with t-butyldiphenylsilyl chloride (32.7 g, 3.3 ME) and 4-dimethylaminopyridine (1 g) at room temperature for 36 h. Tlc (ether-acetone 4:1) revealed the formation of two products. The reaction was worked up by pouring into ice/water and the product was isolated by extraction into ether which was dried (sodium sulphate) and concentrated. The resulting syrup was eluted from a column of silica gel with ether-petrol (4:1) to give initially 6,1',6'-tri-O-(t-butyldiphenylsilyl)sucrose penta-acetate (1.0 g, 27%) followed by 2,3,4,3',4'-penta-O-acetyl-6,6'-di-O-(t-butyldiphenylsilyl)sucrose (25 g, 67%).

(b) Chlorination

A solution of the product of stage (a) (20 g) in pyridine (250 ml) was treated with triphenylphosphine (10.2 g, 2 ME) at room temperature. The mixture was cooled to 0° and carbon tetrachloride (2 ml, 1 ME) was added slowly. The reaction was warmed to room temperature then heated to 70° for 1.5 h. Tlc (ether-petrol 4:1) revealed the formation of a single product, so the reaction was cooled to room temperature, methanol (20 ml) was added, and the solution concentrated to a syrup by co-distillation with toluene. The resulting product was taken up in ether and the triphenylphosphine oxide present allowed to crystallise out. Final purification was achieved by silica gel column chromatography using ether-petrol (1:1) to give 6,6'-di-O-(t-butyldiphenylsilyl)-1'-chloro-1'-deoxysucrose penta-acetate (20 g, 98%).

(c) De-acetylation

De-acetylation was carried out by adding a catalytic amount of sodium methoxide to a solution of the product of stage (b) (20 g) in methanol (200 ml) and stirring the reaction for 4 h at room temperature. The solution was de-ionised by shaking with Amberlyst 15 resin and concentrated to give 6,6'-di-O-(t-butyldiphenylsilyl)-1'-chloro-1'-deoxysucrose (15.5 g, 96%).

(d) Epoxide formation using DIAD and de-silylation

A solution of the product of stage (c) (15 g) in toluene (200 ml) was treated with diisopropylazodicarboxylate (DIAD) (10 ml, 3 ME) and triphenylphosphine (14 g, 3 ME). A mild exothermic reaction was observed and the reaction was quenched by addition of methanol (15 ml) after 0.5 h, and concentrated to a syrup. The triphenylphosphine oxide present crystallised out from ether solution and the resulting product was taken up in thf (200 ml) and treated with 1 M tetra-n-butyl ammonium fluoride (55 ml, 3 ME) at room temperature for 4.5 h. Tlc (ether-petrol 7:1) indicated formation of a single product and so the reaction product was concentrated and then acetylated in pyridine (100 ml) and acetic anhydride (20 ml). After concentration to a syrup, the product was purified by silica gel column chromatography using ether-petrol (1:1) to give 1'-chloro-1'-deoxysucrose 3',4'-lyxo-epoxide penta-acetate (4.5 g, 73%).

(e) Chlorination

A solution of the product of stage (d) (3.5 g) in dmf (40 ml) was treated with lithium chloride (3.5 g) at 80° for 24 h. The reaction was worked up by pouring into ice/water (300 ml) and the product extracted into ether (3×100 ml) which was dried (sodium sulphate) and concentrated. Acetic anhydride (4 ml) and pyridine (30 ml) were then added, the reaction mixture was stirred at room temperature for 4 h and then concentrated to dryness by co-distillation with toluene. The product was purified by column chromatography eluting with ether-petrol (1:1) to give 1',4'-dichloro-1',4'-dideoxysucrose hexa-acetate (2.2 g, 56%).

(f) De-acetylation

A catalytic amount of sodium methoxide was added to a solution of the hexa-acetate (1.5 g) in methanol (70 ml) and the reaction was stirred at room temperature for 4 h. Tlc (ethyl acetate/acetone/water 4:6:1) revealed a single product. The solution was de-ionised with Amberlyst 15 resin and concentrated to give 1',4'-dichloro-1'-4'-dideoxysucrose (0.8 g, 92%).

EXAMPLE 3

4,1',4'-Trichloro-4,1',4'-trideoxygalactosucrose (a) Silylation of 2,3,6,3',4'-penta-O-acetylsucrose (6-PAS)

A solution of 6-PAS (50 g) in dry pyridine (600 ml) was treated with t-butyldiphenylsilyl chloride (30.1 g, 1.1 ME) and 4-dimethylaminopyridine (2 g) at room temperature for 36 h. Methanol was added to destroy excess reagent and the mixture was concentrated to a syrup which was eluted from a column of silica gel using ether-acetone (12:1) to give 6'-O-(t-butyldiphenylsilyl-2,3,6,3',4'-penta-O-acetylsucrose (54 g, 75%).

(b) Chlorination at the 4- and 1'-positions

A solution of the product of stage (a) (24 g, 1 ME) in dry pyridine (250 ml) was treated with triphenyl phosphine (32 g, 4 ME) at room temperature. The mixture was cooled to 0°, carbon tetrachloride (6 ml, 2 ME) was added carefully and the reaction was then heated to 70° for 2 h. Tlc (ether-petrol 4:1) revealed a single product, so the reaction mixture was cooled to 20°, methanol (20 ml) was added and the mixture concentrated to a syrup by codistillation with toluene. The product was dissolved in ether, the triphenylphosphine oxide present crystallised out, and the residue was eluted from a column of silica gel using ether-light pretroleum (1:1) to give 4,1'-dichloro-4,1'-dideoxy-6'-O-(t-butyldiphenylsilyl)-2,3,6,3',4'-penta-O-acetylgalactosucrose (24 g, 96%) as a syrup.

(c) De-acetylation and silyation at C-6

A catalytic amount of sodium methoxide was added to a solution of the product stage (b) (24 g) in dry methanol (200 ml) and the reaction stirred at room temperature for 4 h. The solution was deionised by shaking with Amberlyst 15 (H+) resin and concentrated to give the free sugar as a dry syrup (yield 15 g, 84%) which was used without further purification.

A solution of this product (14 g) in dry pyridine (200 ml) was treated with t-butyldimethylsilyl chloride (7.5 g, 2.2. ME) and 4-dimethylaminopyridine (0.5 g) at room temperature for 36 h. Methanol (20 ml) was added and the reaction concentrated to a syrup which was purified by silica gel column chromatography using ether as the eluent to give 4,1'-dichloro-4, 1'-dideoxy-6'-O-(t-butyldiphenylsily)-6-O-(t-butyldimethylsily)galactosucrose (11 g, 58%).

(d) Formation of the epoxide

A solution of the product of stage (c) (11 g) in ethyl acetate (200 ml) was treated with DEAD (7 ml, 2.6 ME) and triphenylphosphine (4.3 g, 1.3 ME). A mild exothermic reaction was observed and after 1 h, tlc (ether-petrol 7:1) was revealed the formation of one major product. The reaction was quenched by addition of methanol (15 ml) and concentrated to a syrup which was dissolved in ether. The triphenylphosphine oxide was removed by crystallisation and the liquors concentrated to give the lyxo-epoxide as a syrup (7.8 g, 73%).

(e) De-silyation and acetylation

Tetrabutylammonium fluoride (19.2 ml, 3 ME) was added to a solution of the lyxo-epoxide (7 g) in thf (100 ml) at room temperature. After stirring for 5 h, the mixture was concentrated and acetylated by addition of acetic anhydride and pyridine. The resulting product was purified by column chromatography to give 4,1'-dichloro-4,1'-dideoxygalactosucrose-3',4'-lyxo-epoxide tetra-acetate (3.5 g 84%) $[\alpha]_D^{20} + 119.8°$ (c 1.0, CH Cl$_3$).

(f) Chlorination and acetylation

The epoxide (3.5 g) was dissolved in dmf (40 ml) and lithium chloride (3.5 g) was added. The reaction was heated to 80° C. for 24 h and then worked up by pouring into ice/water (200 ml) and extracting into ether (3×100 ml). The organic extracts were dried over sodium sulphate and concentrated to a syrup which was acetylated by addition of pyridine (30 ml) and acetic anhydride (4 ml) at room temperature. After 4 h, the reaction was concentrated to dryness by codistillation with toluene and the product purified by silica gel column chromatography (ether-petrol 1:1) to give 4,1',4'-trichloro-4,1',4'-trideoxygalactosucrose penta-acetate (2.6 g, 60%). $[\alpha]_D^{20} + 83.8°$ (c 1.9, CHCl$_3$).

(g) De-acetylation

A solution of the penta-acetate (2.3 g) in dry methanol (100 ml) was treated with a catalytic amount of sodium methoxide at room temperature for 4 h. Tlc (dichloromethane-methanol, 4:1) revealed a single product. The solution was de-ionised with Amberlyst 15 (H+) resin and concentrated to give 4,1',4'-trichloro-4,1',4'-trideoxygalactosucrose (1.3 g, 78%) which crystallised from acetone-ether. m.p. 125°–126°, $[\alpha]_D^{20} + 72.5°$ (c 1.1, H$_2$O).

Anal. Calc. for C$_{12}$H$_{19}$Cl$_3$O$_8$: C: 36.2; H: 4.77%, Found: C: 36.0; H: 5.41.

EXAMPLE 4

4,4',6'-Trichloro-4,4',6'-trideoxygalactosucrose (a) Chlorination of 6-PAS

6-PAS (27 g) and triphenylphosphine (26 g, 2 ME) were dissolved in dry pyridine (250 ml), the solution was cooled to 0° and carbon tetrachloride (5 ml, 1 ME) was added slowly. The reaction was stirred at 0° for 0.5 h, and then heated to 70° for 2 h. Tlc (ether-acetone 4:1) revealed the presence of a single product and an absence of starting material. The reaction was cooled to 20°, methanol (20 ml) was added and the mixture concentrated to dryness by co-distillation with toluene. The residue was partitioned between water (600 ml) and ethyl acetate (500 ml). The aqueous layer was further extracted with ethyl acetate (2×100 ml) and the organic extracts dried (sodium sulphate) and concentrated to give 6'-chloro-6'-deoxy-2,3,6,3',4'-penta-O-acetylsucrose (24 g, 86%) m.p. 124°–125°.

(b) Silylation

A solution of the 6'-chloro derivative (15 g) in dry pyridine (150 ml) was treated with t-butyldimethylsilyl chloride (9 g, 2.3 ME) and 4-dimethylaminopyridine (200 mg) at 50° for 16 h. Tlc (ether-petrol 10:1) showed one major product. The reaction was cooled to 20°, methanol (20 ml) was added and the mixture concentrated to dryness by co-distillation with toluene. The product was purified by silica gel column chromatography using ether-petrol (2:1) as eluting solvent to give 1'-O-(t-butyldimethylsilyl)-6'-chloro-6'-deoxy-2,3,6,3',4'-penta-O-acetylsucrose (18 g, 89%).

(c) Chlorination and de-acetylation

The product of stage (b) (15 g) and triphenylphosphine (11.5 g, 2 ME) were dissolved in dry pyridine (200 ml) and the solution was cooled to 0°. Carbon tetrachloride (2.4 ml, 1 ME) was added slowly, the reaction was stirred at 0° for 0.5 h, and then heated to 70° for 2 h. Tlc (ether-petrol 4:1) showed a single product. The reaction was worked up as in stage (b) to give 1'-O-(t-butyldimethylsilyl)-4,6'-dichloro-4,6'-dideoxygalactosucrose penta-acetate (15 g, 97%), m.p. 128° (from ether-petrol).

Without further purification, a solution of this dichloride (13 g) in methanol (150 ml) was de-acetylated by treatment with sodium methoxide at room temperature for 4 h. The reaction was worked up by shaking with Amberlyst 15 resin and concentrated to give 1'-O-(t-butyldimethylsilyl)-4,6'-dichloro-4,6'-dideoxygalactosucrose (8.7 g, 96%).

(d) Silylation

A solution of the product of stage (c) (8 g) in pyridine (150 ml) was treated with t-butyldimethylsilyl chloride (5.4 g, 2.2 ME) and 4-dimethylaminopyridine (400 mg) at room temperature for 18 h. The reaction was worked up as described in stage (b) and purified by column chromatography to give 1',6-di-O-(t-butyldimethylsilyl)-4,6'-dichloro-4,6'-dideoxygalactosucrose (8 g, 82%).

(e) Epoxide formation

DEAD (4.2 ml, 3 ME) and triphenylphosphine (7.9 g, 3 ME) were added to a solution of the product of stage (d) (7 g) in ethyl acetate (200 ml) at room temperature, which was then stirred for 30 min. Methanol (10 ml) was added, the mixture was concentrated to a syrup and diethyl ether added. Most of the triphenylphosphine oxide crystallised out and was removed by filtration to give 1',6-di-O-(t-butyldimethylsilyl)-4,6'-dichloro-4,6'-dideoxygalactosucrose 3',4'-lyxo-epoxide (6 g, 88%).

(f) De-silylation and acetylation

A solution of the epoxide (5 g) in thf (100 ml) was treated with 1 M tetrabutylammonium fluoride at room temperature for 5 h. Tlc (ether-petrol 7:1) revealed a single slow-moving product. The mixture was concentrated, dissolved in pyridine (50 ml) and acetic anhydride (10 ml) at 20° for 4 h, and then concentrated again to dryness. The resulting product was purified by column chromatography to give 4,6'-dichloro-4,6'-dideoxygalactosucrose 3'-4'-lyxo-epoxide tetra-acetate (4.3 g, 95%).

(g) Chlorination, acetylation and de-acetylation

Lithium chloride (4 g) was added to the product of stage (f) (4 g) in dmf (40 ml) and the mixture was heated at 80° for 24 h. The reaction was worked up by being poured into ice-water and the product extracted into ether (3×100 ml) which was dried (sodium sulphate) and concentrated. The syrupy product was acetylated with acetic anhydride (4 ml) in pyridine (30 ml) at room temperature for 4 h, and then concentrated to dryness by co-distillation with toluene. The resulting product was purified by column chromatography (ether-petrol 1:1) to give 4,4',6'-trichloro-4,4',6'-trideoxygalactosucrose penta-acetate (4 g, 88%).

A solution of this penta-acetate (3.5 g) in dry methanol (100 ml) was treated with a catalytic amount of sodium methoxide at room temperature for 4 h. Tlc (dichloromethane-methanol 4:1) revealed a single product. The reaction was neutralised by addition of Amberlyst 15 resin, concentrated to dryness and crystallised from acetone-diethyl ether to give 4,4',6'-trichloro-4,4',6'-trideoxygalactosucrose (2 g, 85), $[\alpha]_D^{20}+78.8°$ (c 1.0, H$_2$O).

EXAMPLE 5

4'-Bromo-4,1',6'-trichloro-4,4',1',6'-tetradeoxygalactosucrose(4'-Bromo-TGS)

(a) Bromination (i) A solution of TGS 3',4'-lyxo-epoxide tri-acetate (see Example 1, Route 2, stage (d)) (4 g) in dmf (40 ml) was treated with lithium bromide (6 g) at 80° for 24 h. The reaction was worked up by being poured into ice-/water (300 ml) and the product extracted into ether (3×100 ml), which was then dried (sodium sulphate) and concentrated to a syrup. This was dissolved in pyridine (40 ml) and treated with acetic anhydride (4 ml) at room temperature for 4 h. The reaction mixture was evaporated by co-distillation with toluene to give 4'-bromo-TGS tetra-acetate which was purified by silica gel column chromatography eluting with ether-petrol (1:1). Yield 3.5 g, 70%.

(ii) In an alternative bromination reaction, a solution of the epoxide tri-acetate (4 g) in dichloromethane (40 ml) was treated with hydrobromic acid in acetic acid (45% w/v) (1.4 ml, 1ME) at 0° for 5 min. Pyridine (40 ml) and acetic anhydride (5 ml) were then added and the mixture was stirred at room temperature for 2 h. The reaction was concentrated to dryness by co-distillation with toluene and purified by silica gel column chromatography using ether-petrol 1:1 to give 4'-bromo-TGS tetra-acetate (4 g, 81%).

(b) De-acetylation

De-acetylation of the tetra-acetate (4 g) was carried out by treating its solution in dry methanol (40 ml) with a catalytic amount of sodium methoxide at 0° for 16 h. The solution was de-ionised by stirring with Amberlyst 15 resin and concentrated to dryness. Elution from a short column of silica gel using dichloromethane-methanol (20:1) afforded 4'-bromo-TGS (1.8 g, 61%) which crystallised from acetone-ether. m.p. 78°–80° $[\alpha]_D^{20}+63.4°$ (c 1, H$_2$O).

The reaction of the same epoxide (4 g) in ethanediol (40 ml) with KHF$_2$ (4 g) and NaF (2 g) at 120° for 36 hours, followed by extraction with ethyl acetate, deacetylation and purification as above for the bromo analog gave 4,1',6'-trichloro-4,4',1',6'-tetradeoxy-4'-fluoro galactosucrose (4'-fluoro-TGS) 2.7 g (66%); $[\alpha]_D^{20}+83.2°$ (c 1.1, water); mass spectrum m/e 201, 203, 205 (9:6:1) D$_1$ Cl-mono F-fructose; 181, 183 (mono chlorogalactose); 165 (201-HCl); 165 (181-H$_2$O); sweetness approximately 1,000 times sucrose.

EXAMPLE 6

4,1',4',6'-Tetra bromo-4,1',4',6'-tetradeoxygalactosucrose (a) Bromination of 6-PAS 6-PAS (27.6 g) and triphenylphosphine (78.6 g, 6 ME) were dissolved in pyridine (300 ml) at room temperature then cooled to 0°. Carbon tetrabromide (50 g, 3 ME) was added with stirring and the reaction heated to 75° for 4 h.

Methanol (50 ml) was added to the cooled reaction mixture to destroy excess triphenylphosphine and the resulting solution evaporated to a syrup which was taken up in dichloromethane. This solution was washed successively with water, 1 M HCl, aqueous sodium bicarbonate and water, the organic extracts then being dried over sodium sulphate, filtered through charcoal and concentrated. The resulting syrup was stirred with diethyl ether to give a crystalline precipitate of triphenylphosphine oxide which was filtered off. The filtrate was evaporated and the residue dissolved in ethanol from which 4,1',6'-tribromo-4,1',6'-trideoxygalactosucrose penta-acetate (18.5 g, 50%) was obtained crystalline.

(b) De-acetylation of 4,1',6'-tribromo-4,1',6'-trideoxygalactosucrose penta-acetate A solution of the above product in methanol was treated with sodium methoxide to pH 9.5–10 at room temperature for 4 h, neutralised by addition of Amberlyst 15(H)+ resin, filtered and concentrated to a dry foam. Yield 12 g (91%).

(c) Silylation of 4,1',6'-tribromo-4,1',6'-trideoxygalactosucrose

A solution of 4,1',6'-tribromo-4,1',6'-trideoxygalactosucrose (18 g) in pyridine (100 ml) was treated with t-butyldimethylsilyl chloride (11.3 g, 2.2 ME) and 4-N,N-dimethylaminopyridine (2.6 g, 0.6 ME) and the mixture heated to 70° for 2 h. The reaction was poured into ice-water and the water decanted away from the syrupy residue which was dissolved in diethyl ether, dried (sodium sulphate) and eluted from a column of silica gel using diethyl ether. The resulting product, 4,1',6'-tribromo-4,1',6'-trideoxy-6-O-t-butyldimethylsilylgalactosucrose (13 g, 60%) was isolated as a dry syrup.

(d) Formation of the epoxide

DEAD (9.6 g, 2.8 ME) and triphenylphosphine (15 g, 2.8 ME) were added to a solution of the above product (13 g) in toluene (100 ml). The reaction was stirred for 10 min. at room temperature, and then methanol (20 ml) was added and the mixture evaporated to give 4,1',6'-tribromo-4,1',6'-trideoxy-6-O-t-butyldimethylsilylgalactosucrose 3',4'-lyxo-epoxide which was used without further purification.

(e) De-silylation and acetylation

The syrupy epoxide produced above was dissolved in thf (150 ml) and to this solution was added 20 ml (1.5 ME) of a 1 M solution of tetrabutylammonium fluoride in thf. The mixture was left for 2 h at room temperature and then evaporated and treated with acetic anhydride and pyridine at room temperature for 16 h. Methanol was added to destroy excess acetic anhydride and the mixture evaporated. The residue was dissolved in dichloromethane which was washed successively with water, 1 M HCl, aqueous sodium bicarbonate and water, then dried over sodium sulphate, filtered and evaporated. The resulting syrup was eluted through a column of silica gel using ether-petrol 1:1 to give 4,1',6'-tribromo-4,1',6'-trideoxygalactosucrose 3',4'-lyxo-epoxide tri-acetate (6.4 g, 49%).

(f) Opening the epoxide ring with bromide followed by acetylation

A solution of the epoxide (1.7 g) in dichloromethane (15 ml) was treated with 45% HBr in acetic acid (0.6 ml, 1.2 ME) and the reaction left at room temperature for 20 min. Pyridine (10 ml) and acetic anhydride (2 ml) were added and the mixture left at room temperature for 2 h. Methanol (2 ml) was added and the reaction mixture was concentrated to a syrup which was taken up in dichloromethane. This solution as washed with water, 1 M HCl, aqueous sodium bicarbonate and water, then dried (sodium sulphate), filtered and concentrated. The residue crystallised from ether-petrol to give 4,1',4',6'-tetrabromo-4,1',4',6'-tetradeoxygalactosucrose tetra-acetate (1.4 g, 70%).

(g) De-acetylation

A solution of the tetra-acetate (1.4 g) in dry methanol was treated with 1 M sodium methoxide to pH 8.5 and the mixture cooled to −5° for 10 h. Two products, one major and one minor were observed by tlc. The solution was neutralised with Amberlyst 15(H+) resin, then filtered and evaporated. The residue was eluted through a column of silica gel using dichloromethane/methanol (20:1) to give 0.8 g of the major product. Crystallisation and recrystallisation from diethyl ether gave 4,1',4',6'-tetrabromo-4,1',4',6'-tetradeoxygalactosucrose (0.65 g, 60%), m.p. 72°–76°, $[\alpha]_D^{20} + 58.3°$ (c 0.75, $H_2O$).

EXAMPLE 7

1',4',6'-Trichloro-1',4',6'-trideoxysucrose

(a) Chlorination of 6-PAS

6-PAS (54.9 g) was dissolved in pyridine (500 ml) and triphenylphosphine (48.9 g) was added into the solution. When on shaking the solution became clear, the mixture was cooled to 0° C. in an ice bath. Carbon tetrachloride (9 ml) was added into the reaction mixture and it was allowed to come to the room temperature. After keeping it at the room temperature for 30 minutes, the mixture heated at 60° for 1 hr. Tlc (5:1-ether:petrol) showed one major product which had an Rf value similar to an authentic sample and a minor faster product.

Methanol was added to the reaction mixture and it was concentrated to a syrup which was portioned between ether and water. The other layer was dried ($Na_2SO_4$) and eluted from a column of silica gel using 1:1 ether:petrol mixture. Yield: 30 g of 2,3,6,3',4'-penta-O-acetyl-6'-chloro-6'-deoxysucrose.

(b) Silylation t-Butyldiphenylchlorosilane (14.35 ml) was added to a solution of the product of stage (a) (27 g) in pyridine (300 ml). After the addition of 4-dimethylaminopyridine catalyst (100 mg), the mixture was heated at 60° C. for 16 hrs. Tlc in ether indicated very little reaction ~30%. At this stage further t-BDPSCl (5 ml) and catalyst (10 mg) was added to the reaction mixture and heating continued for 24 hours. Tlc indicated nearly 50% reaction and only one product was formed. The reaction mixture was concentrated and eluted from a column of silica gel using first petrol (~2L) and then ether/petrol, 1.5:1, giving the pure 1'-silyl ether (8.0 g), which was acetylated using acetic-anhydride-pyridine, to afford the hexaacetate (8.0 g).

(c) De-silylation

A solution of the product of stage (b) (7.5 g) in thf (35 ml) was desilylated using tetrabutylammonium fluoride (7 ml) at room temperature for 18 hrs. Tlc (ether:petrol 6:1) indicated 80% disilylation. Another 3 ml, quantity of T.BUAF was added to the reaction mixture, which was left to stir for a further 8 hrs. Tlc then indicated the presence of one major product. After concentration, the mixture was eluted from a column of silica gel using petrol first and then ether:petrol 1:1 obtaining pure 2,3,4,6,3',4'-hexa-O-acetyl-6'-chloro-6'-deoxy sucrose (5.0 g, 88% yield).

(d) Chlorination

The hexaacetate was chlorinated using the conditions of stage (a). After column chromatography, the mixture gave 2,3,4,6,3',4'-hexa-O-acetyl-1',6'-dichloro 1',6'-dideoxy sucrose which was then deacetylated using $CH_3ONa$ to afford pure 1',6'-dichloro-1',6'-dideoxy sucrose crystallized from ethylacetate.

(e) Silylation

A solution of the 1',6'-dichloro material (5.7 g) in pyridine (50 ml) was silylated using t-butyldiphenylsilyl chloride in the presence of 4-dimethylaminopyridine (100 mg) at 60° C. for 16 h. Tlc (ethyl acetate:acetone:water: 6:8:1) showed there was no starting material left.

The reaction mixture which had some faster and slower impurities was acetylated with acetic anhydride/pyridine and then eluted from a column of silica gel using ether:petrol 1:1. The product was then deacetylated using sodium methoxide to give the pure 6-t-butyldiphenylsilyl ether (6.0 g).

(f) Epoxidation

Triphenylphosphine (9.1 g) was added to a solution of the product of stage (e) (7.0 g) and diethylazodicarboxylate (6.12 ml) in pyridine (50 ml). The reaction mixture became warm almost immediately and remained warm for about 5 minutes. Tlc ether:petrol showed one major product and some minor faster products. The reaction mixture, after the addition of methanol (10 ml) was concentrated to a syrup which was acetylated with acetic anhydride/pyridine for 6 hrs. It was then concentrated and on column chromatography eluting with ether:petrol 1:1 yielded the 3',4'-epoxide (4.5 g).

(g) Desilylation

A sample of the epoxide (4.0 g) was desilylated with tetrabutylammoniumfluoride as in stage (c). After concentration, the reaction mixture was 6-acetylated using acetic anhydride/pyridine. On work up, tlc (ether:petrol, 4:1) showed one major product. Column chromatography of the reaction mixture using ether:petrol; 1:1 afforded the pure tetraacetate (2.75 g).

(h) Ring opening with lithium chloride

Lithium chloride (3.0 g) was added to a solution of the product of stage (g) (2.6 g) in DMF (15 ml) and the contents were heated at 120° C. for 24 hours. The reaction mixture after concentration was acetylated in the usual way. It was then dissolved in ether and very carefully washed with water 3 times. The water was extracted with ether 3 times. The ether extracts were then dried, filtered and concentrated. Elution from a column of silica gel using ether:petrol as eluant afforded 1',4',6'-trichloro-1',4',6'-trideoxysucrose pentaacetate (2.0 g).

(i) Deacetylation and purification

A solution of the pentaacetate (1.7 g) in methanol (15 ml) was deacetylated with sodium methoxide for 10 hrs. Tlc (ethyl/acetate:acetone:water: 6:8:1) showed one major product. The reaction mixture was neutralised, filtered, concentrated and was column chromatographed on silica gel. Elution with ethyl/acetate afforded pure 1',4',6'-trichloro-1',4',6'-trideoxysucrose (750 mg)

EXAMPLE 8

4'-Iodo-4,1',6'-trichloro-4,1',4',6'-tetradeoxygalactosucrose (4'-iodo-TGS)

(a) De-acetylation and etherification

TGS 3',4'-lyxo-epoxide tri-acetate (20 g) was treated with sodium methoxide and methanol to pH 9 for 4 h. The solution was neutralised with Amberlyst resin, concentrated to dryness, and the residue was dissolved in dichloromethane (200 ml). Dihydropyran (50 ml) and pyridinium tosylate (5 g) were added and the reaction stirred at room temperature for 3 h. Amberlite IR4-5(OH−) resin was added to neutralise the reaction mixture which was filtered, washed twice with water, dried (Na2SO4) and concentrated to a syrup of TGS 3',4'-lyxoepoxide tri-tetrahydropyranyl ether.

(b) Reaction of epoxide with methyl magnesium iodide

TGS 3',4'-lyxoepoxide tri-tetrahydropyranyl ether (12.1 g) in diethyl ether (100 ml) was added to a Grignard reagent prepared from magnesium (1 g) and methyl iodide (7.5 g) in diethyl ether (100 ml) with vigorous stirring. The reaction was heated under reflux for 3 h and then saturated ammonium chloride solution was added slowly. The ether layer was separated out, dried over sodium sulphate, filtered and evaporated to give 12.5 g of syrupy product. This was dissolved in methanol (150 ml), pyridinium tosylate (2.5 g) was added and the reaction left at room temperature for 2 days. After neutralisation, the solution was concentrated and eluted through a column of silica gel with ether-acetone 1:1 to give 4'-iodo-TGS which was characterised by nmr and mass spectrometry as its tetra-acetate.

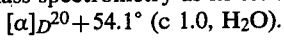

EXAMPLE 9

4-Chloro-1',4',6'-tribromo-4,1',4',6'-tetradeoxygalactosucrose (a) Tritylation of 6-PAS A solution of 6-PAS (50 g) in pyridine (450 ml) was treated with trityl chloride (100 g) at 80° for 8 h. The reaction was cooled, poured into ice/water and the product extracted into dichloromethane which was dried and concentrated to a syrup consisting predominantly of 2,3,6,3',4'-penta-O-acetyl-1',6'-di-O-tritylsucrose.

(b) Chlorination

The product from (a) was dissolved in pyridine (400 ml), triphenylphosphine (50 g) and carbon tetrachloride (15 ml) were added and the reaction heated to 70° for 2 h. The solution was concentrated to a syrup by co-distillation with toluene, and the resulting product was taken up in ether. Triphenylphosphine oxide crystallised out and was filtered off, and the remaining solution was concentrated to dryness.

(c) De-tritylation

The product from (b) was dissolved in acetic acid (750 ml) and water (15 ml) and heated to 120° for 1 h, then cooled and evaporated to dryness. The product was isolated by silica gel column chromatography (ether) to give 2,3,6,3',4'-penta-O-acetyl-4-chloro-4-deoxygalactosucrose (6.2 g).

(d) Bromination

The product from (c) (6.2 g) was dissolved in pyridine (100 ml) and triphenylphosphine (11.4 g) and carbon tetrabromide (7.3 g) were added at room temperature. The reaction was heated to 80° for 2 h, then cooled, and after addition of methanol (20 ml), was concentrated to a syrup which consisted predominantly of 1',6'-dibromo-4-chloro-4,1',6'-trideoxygalactosucrose penta-acetate.

(e) De-acetylation

The penta-acetate from (d) was de-acetylated in the usual way with sodium methoxide in methanol to give 1',6'-dibromo-4-chloro-4,1',6'-trideoxygalactosucrose (4.0 g).

(f) Silylation

A solution of the product from (e) (4.0 g) in pyridine (20 ml) was treated with t-butyldiphenylsilyl chloride (5 g) and 4-dimethylaminopyridine (about 200 mg) at room temperature for 36 h. The reaction was worked up by pouring into ice/water and the product isolated by extraction into ether which was dried (Na$_2$SO$_4$) and concentrated to give 1',6'-dibromo-6-O-t-butyl-diphenylsilyl-4-chloro-4,1',6'-trideoxygalactosucrose (4.0 g).

(g) Epoxide formation

The product from (e) (4.0 g) in toluene (50 ml) was treated with DEAD (2.5 ml) and triphenylphosphine (3.5 g) at about 30° for 0.5 h. Methanol (5 ml) was added to quench the reaction which was concentrated to a syrup. Ether was added and the triphenylphosphine oxide present crystallised out. The resulting solution was concentrated, taken up in thf (40 ml) and treated with tetra-n-butyl ammonium fluoride (15 ml) at room temperature for 5 h. The reaction was concentrated and acetylated using acetic anhydride and pyridine in the usual way to give 1',6'-dibromo-4-chloro-4,1',6'-trideoxygalactosucrose 3',4'-lyxoepoxide tri-acetate (1.5 g).

(h) Bromination

A solution of the product from (g) (1.5 g) in dichloromethane (20 ml) was treated with hydrogen bromide in acetic acid (45%) (1.0 g) at room temperature for 30 minutes. The reaction was worked up by pouring into ice/water and the product was extracted into ether which was dried and concentrated. The product was acetylated and worked up in the usual way to give 1',4',6'-tribromo-4-chloro-4,1',4',6'-tetradeoxygalactosucrose tetra-acetate (1.0 g).

(f) De-acetylation

The tetra-acetate from (h) (1.0 g) was de-acetylated with sodium methoxide in methanol in the usual way to give 1',4',6'-tribromo-4-chloro-4,1',4',6'-tetradeoxygalactosucrose (0.5 g, 97%); $[\alpha]_D^{20}+63.9°$ (c 0.3, H$_2$O).

EXAMPLE 10

1',4',6'-trichloro-4,1',4',6'-tetradeoxy-4-fluorogalactosucrose

(a) 1',6'-Dichloro-1',6'-dideoxysucrose pentaacetate 2,3,6,3',4'-Penta-O-acetylsucrose (45 g) was dissolved in pyridine (340 ml) at room temperature. Triphenylphosphine (78 g) was added with stirring and the solution cooled to 5° C. Carbon tetrachloride (25 g) was slowly added, maintaining the reaction temperature below 10° C. The solution was stirred at room temperature for 0.5 h and then at 40° C. for 48 h. Methanol (200 ml) and carbon tetrachloride (20 ml) were added and the mixture evaporated to dryness, followed by evaporation with toluene (twice). The residue was dissolved in dichloromethane (300 ml), washed with dilute hydrochloric acid, saturated sodium bicarbonate and water, dried (sodium sulphate), decolourised (charcoal), filtered and evaporated to a syrup. The syrup was chromatographed on silica gel, eluting with ether-petrol (bp 40°-60° C.) (8:1), to yield the product as a solid, recrystallised from ether-petrol. Yield 18 g.

(b) 1',6'-Dichloro-4,1',6'-trideoxy-4-fluorogalactosucrose

The above dichloro sucrose pentaacetate (10 g) was dissolved in a mixture of pyridine (1.5 ml) and dichloromethane (15 ml), and slowly added to a solution of diethylaminosulphur trifluoride (3.2 g) in a mixture of pyridine (1.5 ml) and dichloromethane (15 ml). The solution was stirred at room temperature for 48 h and evaporated to dryness at 65° C. Toluene was added to the residue and the mixture evaporated to dryness (2×). The residue was chromatographed in silica gel, eluting with ether-petrol (3:1). The solid product was deacetylated with M-sodium methoxide (0.5 ml) in methanol (30 ml) at pH9 for 1 h at room temperature. The methanolic solution was deionised with ion-exchange resin (Zeolit-DMF, H$^+$/CO$_3^{2-}$), filtered and evaporated to dryness to yield the product as a white foam.

(c) 3,4-Anhydro-1,6-dichloro-1,6-dideoxy-β-D-tagatofuranosyl 4-deoxy-4-fluoro-α-D-galactopyranoside The dichlorofluorogalactosucrose (1 g) was dissolved in tetrahydrofuran (8 ml) and triphenylphosphine (2 g) added with stirring. The solution was cooled to 0° C. and diethylazodicarboxylate (1.4 g) in tetrahydrofuran (2 ml) added slowly while maintaining the temperature below 5° C. After the addition, the reaction mixture was kept at room temperature for 2 h when tlc (dichloromethane-methanol, 5:1) showed the reaction to be complete. Water (1 ml) was added and the mixture evaporated to dryness at 40° C. The residue was extracted with water (3×10 ml), filtered and washed with water. The combined aqueous extracts and washings was washed with dichloromethane (2×20 ml) and the aqueous solution evaporated to dryness. The residue was chromatographed on silica gel, eluting with ether-acetone (4:1). The product was isolated as a white foam. Yield 0.8 g.

(d) 1,4',6'-Trichloro-4,1',4',6'-tetradeoxy-4-fluorogalactosucrose

The epoxide (0.6 g) was dissolved in acetone (6 ml) and lithium chloride (600 mg) and 2 M hydrochloric acid (1.2 ml) added. The mixture was stirred under reflux for 2 h, when tlc (ether-acetone 4:1) showed the reaction to be complete. The solution was neutralised by addition of solid sodium bicarbonate and the resulting mixture was evaporated to remove acetone. The residue was extracted with ethyl acetate (3×10 ml) and the combined ethyl acetate extracts washed with saturated brine, dried (magnesium sulphate), filtered and evaporated. The resulting foam was dissolved in ether and the product crystallised by addition of petrol. The product was recrystallised from ether-petrol and obtained as a white crystalline solid (0.3 g), m.p. 57°-58° C.; mass spectrum m/e 217, 219, 221, 223, (27:27:9:1, trichlorofructose), 165 (monofluorogalactose), 182, 184, 186 (9:6:1, 217, 219, 221-Cl), 147 (165-H$_2$O). $[\alpha]_D^{20}+55.1$ (c 0.79, methanol).

EXAMPLE 11

Reduced calorie cola drink containing sugar

Ingredients to prepare 100 ml bottling syrup:

| | |
|---|---|
| 4'-bromo-4,1',6'-trichloro-4,1',4',6'-tetradeoxy-galactosucrose (Compound 1) | 13.5 mg |
| sucrose | 60 g |
| benzoic acid | 35 mg |
| phosphoric acid (conc) | 1 ml |
| cola flavour | 1.1 ml |
| colour | ad lib. |
| mineral water | ad 100 ml |

This syrup may then be added in 20 ml doses to carbonated 225 ml aliquots of chilled mineral water.

EXAMPLE 12

Sweetening tablets for beverages

Each tablet contains:

| | |
|---|---|
| Compound 1 | 1.34 mg |
| or | |
| Compound 2 | 0.53 mg | together with a dispersible tablet base (ca. 60 mg) containing sucrose, gum arabic and magnesium stearate, and is equivalent in sweetness to about 4.5 g sucrose.

EXAMPLE 13

Bulked sweetener

A bulked sweetener having the same sweetness as an equivalent volume of sucrose (granulated sugar) is prepared by mixing the following ingredients and spray-drying to a bulk density of 0.2 g/cc.

| | |
|---|---|
| maltodextrin solution containing dry weight | 222.2 g |
| Compound 3 | 5.0 g |
| or | |
| Compound 1 | 0.34 g |

The resulting composition has a sweetening power equivalent to approximately 2 kilograms of sugar.

EXAMPLE 14

Carbonated low calorie lemonade (sugar free)

Ingredients to prepared 100 ml syrup:

| | |
|---|---|
| Compound 2 | 5 mg |
| or | |
| Compound 4 | 237 mg |
| Benzoic acid | 35 mg |
| Citric acid (dry base) | 1.67 g |
| Lemon essence | 0.8 g |
| Make up to 100 ml in mineral water. | |

This syrup can be added in 25 ml doses to 225 ml aliquots of carbonated chilled mineral water.

EXAMPLE 15

Toothpaste

| | % by weight |
|---|---|
| Dibasic calcium phosphate | 50% |
| Glycerol | 20% |
| Sodium lauryl sulphate | 2.5% |
| Spearmint oil | 2.5% |
| Gum tragacanth | 1.0% |
| Compound 1 | 0.006% |

-continued

| | % by weight |
|---|---|
| Water | 23.99% |

The ingredients are mixed to produce a spearmint flavoured toothpaste of acceptable sweetness but free from sugar or saccharin.

EXAMPLE 16

Chewing Gum

| | part by weight |
|---|---|
| Polyvinyl acetate | 20 |
| Butyl phthalylbutylglycolate | 3 |
| Polyisobutylene | 3 |
| Microcrystalline wax | 2 |
| Calcium carbonate | 2 |
| Flavouring/aroma | 1 |
| Compound 2 | 0.0056 |
| Glucose | 10 |

The above chewing gum base can be cut into convention tablets or strips.

I claim:

1. A compound of the formula (I)

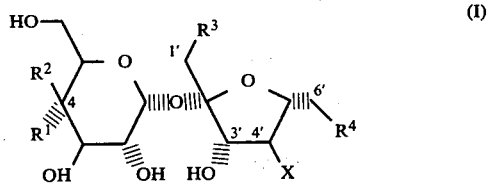

wherein

X represents a halogen atom;

$R^1$ and $R^2$ respectively represent a combination selected from the group consisting of: a hydroxy group and a hydrogen atom; a halogen atom and a hydrogen atom; and a hydrogen atom and a halogen atom; and $R^3$ and $R^4$ independently represent a substituent selected from the group consisting of a halogen atom and a hydroxy group;

at least one of $R^1$, $R^2$ and $R^3$ representing a halogen atom.

2. A compound according to claim 1, wherein $R^2$ represents a halogen atom.

3. A compound according to claim 2, wherein $R^2$, $R^3$, $R^4$ and X all represent halogen atoms.

4. A compound according to claim 1 selected from the group consisting of:

4'-Bromo-4,1',6'-trichloro-4,1',6'-tetradeoxygalactosucrose;

4,1',4',6'-Tetrabromo-4,1',4',6'-tetradeoxygalacosucrose;

4,1',4'-Trichloro-4,1',4'-trideoxygalactosucrose;

4,4',6'-Trichloro-4,4',6'-trideoxygalactosucrose;

1',4',6'-Trichloro-1',4',6'-trideoxysucrose;

1,4,6-Tribromo-1,4,6-trideoxy-β-D-fructofuranosyl 4-chloro-4-deoxy-α-D-galactopyranoside;

1,6-Dichloro-1,4,6-trideoxy-4-iodo β-D-fructofuranosyl 4-chloro-4-deoxy-α-D-galactopyranoside;

1,4-Dichloro-1',4'-dideoxysucrose; and 1,4,6-Trichloro-1,4,6-trideoxy-β-D-fructofuranosyl 4-deoxy-4-fluoro-α-D-galactopyranoside.

5. The compound according to claim 1, which is 4,1',4',6-tetrachloro-4,1',4',6'-tetradeoxygalactosucrose.

6. An ingestible product or oral composition containing at least one compound according to claim 1 in an effective amount as a sweetener.

7. A product or composition according to claim 6 containing a compound selected from the group consisting of:
- 4'-Bromo-4',1',6'-trichloro-4,1',4',6'-tetradeoxygalactosucrose;
- 4,1',4',6'-Tetrabromo-4,1',4',6'-tetradeoxygalacosucrose;
- 4,1',4'-Trichloro-4,1',4'-trideoxygalactosucrose;
- 4,4',6'-Trichloro-4,4',6'-trideoxygalactosucrose;
- 1',4',6'-Trichloro-1',4',6'-trideoxysucrose;
- 1,4,6-Tribromo-1,4,6-trideoxy-β-D-fructofuranosyl 4-chloro-4-deoxy-α-D-galactopyranoside;
- 1,6-Dichloro-1,4,6-trideoxy-4-iodo β-D-fructofuranosyl 4-chloro-4-deoxy-α-D-galactopyranoside;
- 1',4'-Dichloro-1',4'-dideoxysucrose; and
- 1,4,6Trichloro-1,4,6-trideoxy-β-D-fructofuranosyl 4-deoxy-4-fluoro-α-D-galactopyranoside.

8. A product or composition according to claim 6 containing 4,1',4',6'-tetrachloro-4,1',4',6'-tetradeoxy galactosucrose.

9. A sweetening composition containing a compound according to claim 1 together with a carrier therefor.

10. A sweetening composition according to claim 9 containing a compound selected from the group consisting of:
- 4'-Bromo-4',1',6'-trichloro-4,1',4',6'-tetradeoxygalactosucrose;
- 4,1',4',6'-Tetrabromo-4,1',4',6'-tetradeoxygalacosucrose;
- 4,1',4'-Trichloro-4,1',4'-trideoxygalactosucrose;
- 4,4',6'-Trichloro-4,4',6'-trideoxygalactosucrose;
- 1',4',6'-Trichloro-1',4',6'-trideoxysucrose;
- 1,4,6-Tribromo-1,4,6-trideoxy-β-D-fructofuranosyl 4-chloro-4-deoxy-α-D-galactopyranoside;
- 1,6-Dichloro-1,4,6-trideoxy-4-iodo β-D-fructofuranosyl 4-chloro-4-deoxy-α-D-galactopyranoside;
- 1',4'-Dichloro-1',4'-dideoxysucrose; and
- 1,4,6-Trichloro-1,4,6-trideoxy-β-D-fructofuranosyl 4-deoxy-4-fluoro-α-D-galactopyranoside.

11. A sweetening composition according to claim 9 containing 4,1',4',6'-tetrachloro-4,1',4',6'-tetradeoxy galactosucrose.

12. A method of sweetening a substance comprising incorporating therein as a sweetener an effective amount of a compound according to claim 1.

* * * * *